(12) United States Patent
Spence et al.

(10) Patent No.: US 11,439,726 B2
(45) Date of Patent: Sep. 13, 2022

(54) SURGICAL IMPLANTS

(71) Applicant: OsseoMimetic, LLC, Wynnewood, PA (US)

(72) Inventors: Trevor B. Spence, Capitola, CA (US); John L. Ricci, Middletown, NJ (US)

(73) Assignee: OsseoMimetic, LLC, Wynnewood, PA (US)

( * ) Notice: Subject to any disclaimer, the term of this patent is extended or adjusted under 35 U.S.C. 154(b) by 59 days.

(21) Appl. No.: 16/701,840

(22) Filed: Dec. 3, 2019

(65) Prior Publication Data
US 2020/0171202 A1 Jun. 4, 2020

Related U.S. Application Data

(60) Provisional application No. 62/774,860, filed on Dec. 3, 2018.

(51) Int. Cl.
*A61F 2/44* (2006.01)
*A61F 2/28* (2006.01)
(Continued)

(52) U.S. Cl.
CPC .......... *A61L 27/18* (2013.01); *A61B 17/0401* (2013.01); *A61B 17/8061* (2013.01); *A61B 17/8625* (2013.01); *A61F 2/30771* (2013.01); *A61F 2/34* (2013.01); *A61F 2/3609* (2013.01); *A61F 2/389* (2013.01); *A61F 2/3859* (2013.01); *A61F 2/4225* (2013.01); *A61F 2/4241* (2013.01); *A61F 2/4405* (2013.01);
(Continued)

(58) Field of Classification Search
CPC .. A61L 27/18; A61F 2/30771; A61F 2/30767;
A61F 2/0077; A61F 2/28; A61F 2/44;
A61F 2/4455; A61F 2002/3082; A61F
2002/30822; A61F 2002/30827; A61F
2002/30828; A61F 2002/30838; A61F
2002/30864; A61F 2002/3093; A61F
2002/0081; A61F 2002/0086
See application file for complete search history.

(56) References Cited

U.S. PATENT DOCUMENTS 6,419,491 B1 7/2002 Ricci et al.
8,414,654 B1 4/2013 Ganey
(Continued)

OTHER PUBLICATIONS

Albrektsson, T. et al., "Osteoinduction, osteoconduction and osseointegration," European Spine Journal, Jun. 2001, pp. 96-101, Springer-Verlag.
(Continued)

*Primary Examiner* — David H Willse
(74) *Attorney, Agent, or Firm* — Mendelsohn Dunleavy, P.C.; Steve Mendelsohn

(57) ABSTRACT

A surgical implant having a plastic (e.g., PEEK) component having an exposed surface, wherein at least a portion of the exposed surface has a plurality of parallel microgrooves that (i) enhance bone growth and osseointegration with adjacent bone and, after the osseointegration, (ii) increase pull-out force of the surgical implant from the adjacent bone. In certain embodiments, the microgrooves have widths of less than or equal to 12 micrometers, depths of less than or equal to 12 micrometers, crests of less than or equal to 12 micrometers, and a periodicity of less than or equal to 24 micrometers.

11 Claims, 13 Drawing Sheets

(51) Int. Cl.
| | |
|---|---|
| A61B 17/86 | (2006.01) |
| A61L 27/18 | (2006.01) |
| A61F 2/80 | (2006.01) |
| A61F 2/36 | (2006.01) |
| A61F 2/34 | (2006.01) |
| A61F 2/38 | (2006.01) |
| A61F 2/42 | (2006.01) |
| A61B 17/04 | (2006.01) |
| A61B 17/80 | (2006.01) |
| A61F 2/30 | (2006.01) |
| A61L 31/06 | (2006.01) |
| A61B 17/00 | (2006.01) |
| A61F 2/00 | (2006.01) |

(52) U.S. Cl.
CPC .......... *A61F 2/447* (2013.01); *A61F 2/4455* (2013.01); *A61F 2/80* (2013.01); *A61L 31/06* (2013.01); *A61B 2017/00955* (2013.01); *A61B 2017/044* (2013.01); *A61F 2002/0081* (2013.01); *A61F 2002/0086* (2013.01); *A61F 2002/3093* (2013.01); *A61F 2002/30822* (2013.01); *A61F 2002/30828* (2013.01); *A61F 2002/3611* (2013.01); *A61F 2002/4251* (2013.01); *A61F 2002/4256* (2013.01); *A61L 2400/18* (2013.01); *A61L 2430/02* (2013.01); *A61L 2430/24* (2013.01); *A61L 2430/38* (2013.01)

(56) References Cited

U.S. PATENT DOCUMENTS

| | | | |
|---|---|---|---|
| 8,821,912 | B2 | 9/2014 | Crudden et al. |
| 8,840,914 | B2 | 9/2014 | Crudden et al. |
| 9,107,765 | B2 | 8/2015 | Ghiselli et al. |
| 9,132,576 | B2 | 9/2015 | Crudden et al. |
| 9,375,321 | B2 | 6/2016 | Whang et al. |
| 9,492,584 | B2 | 11/2016 | Crudden et al. |
| 9,848,995 | B2 * | 12/2017 | Ullrich, Jr. ............ A61F 2/4611 |
| 9,908,296 | B2 | 3/2018 | Chang et al. |
| 10,322,209 | B2 | 6/2019 | Knaack et al. |
| 2001/0039454 | A1 * | 11/2001 | Ricci ........................ A61F 2/32 623/23.5 |
| 2005/0119758 | A1 * | 6/2005 | Alexander .......... A61F 2/30771 623/23.5 |
| 2012/0141599 | A1 | 6/2012 | Johns et al. |
| 2012/0315340 | A1 | 12/2012 | Crudden et al. |
| 2013/0004585 | A1 | 1/2013 | Crudden et al. |
| 2013/0037991 | A1 | 2/2013 | Crudden et al. |
| 2013/0073042 | A1 | 3/2013 | Ghiselli et al. |
| 2014/0035201 | A1 | 2/2014 | Jarman-Smith et al. |
| 2020/0323646 | A1 * | 10/2020 | Picha .................... A61F 2/4455 |

OTHER PUBLICATIONS

Sul, Young-Taeg et al.,"Optimum Surface Properties of Oxidized Implants for Reinforcement of Osseointegration: Surface Chemistry, Oxide Thickness, Porosity, Roughness, and Crystal Structure," The International Journal of Oral & Maxillofacial Implants, May 2005, pp. 349-359, vol. 20, No. 3, Quintessence Publishing Co, Inc.

Chen, Yu et al., "Comparison of titanium and polyetheretherketone (PEEK) cages in the surgical treatment of multilevel cervical spondylotic myelopathy: a prospective, randomized, control study with over 7-year follow-up," European Spine Journal, Apr. 2013, pp. 1539-1546, Springer-Verlag, Berlin Heidelberg.

Gittens, Rolando A. et al., "Implant Osseointegration and the Role of Microroughness and Nanostructures: Lessons for Spine Implants," NIH Public Access Author manuscript, Acta Biomater, Aug. 2014, pp. 1-22, Elsevier Ltd.

Ricci, John et al., "Cell Response to Surfaces: A Concise Summary," The International Journal of Periodontics & Restorative Dentistry, 2016, pp. s38-s46, vol. 36, Supplement, Quintessence Publishing Co, Inc.

Johansson, Pär et al., "Polyether ether ketone implants achieve increased bone fusion when coated with nano-sized hydroxyapatite: a histomorphometric study in rabbit bone," International Journal of Nanomedicine, Apr. 2016, pp. 1-15, Dove Medical Press Limited.

Ma, Rui et al.,"Current Strategies to Improve the Bioactivity of PEEK," International Journal of Molecular Sciences, Mar. 2014, pp. 5426-5445, MDPI, Basel, Switzerland.

Pendegrass, Catherine J. et al., "Development of a soft tissue seal around bone-anchored transcutaneous amputation prostheses," Biomaterials 27, Apr. 2006, pp. 4183-4191, Elsevier Ltd.

Chimutengwende-Gordon, M. et al., "The Intraosseous Transcutaneous Amputation Prosthesis (ITAP): Optimization of fibroblast adhesion to fibronectin silanized titanium alloy," 55th Annual Meeting of the Orthopaedic Research Society, Poster No. 494, Feb. 2009, p. 1, Las Vegas, NV.

Cordero, D et al., "In vitro response of pre-osteoblastic cells to laser microgrooved PEEK," Biomedical Materials, Sep. 2013, pp. 1-8, IOP Publishing Ltd.

Toth, Jeffrey M., "Polyetheretherketone as a Biomaterial for Spinal Applications," Biomedical Engineering Faculty Research and Publications, Jan. 2006, pp. 1-16, e-Publidations@Marquette.

Di Silvio, L. et al, "Cellular response to osteoinductive materials in orthopaedic surgery," Cellular Response to Biomaterials, 2009, pp. 313-343, Woodhead Publishing Ltd., Cambridge, UK.

* cited by examiner

100

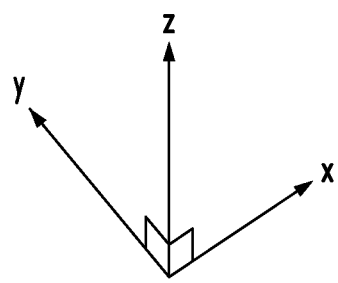
FIG. 2
200
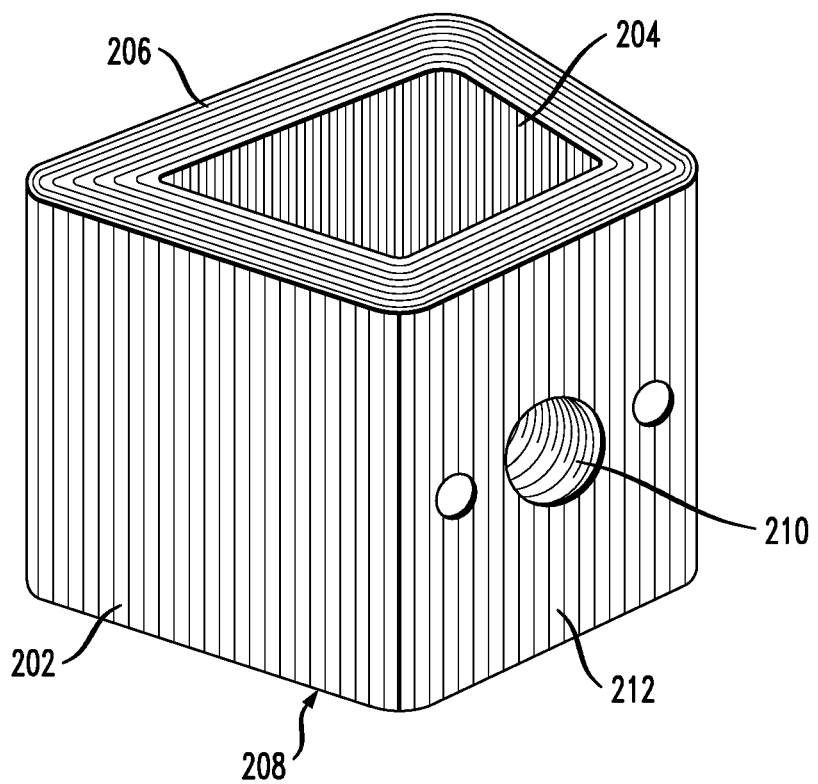

400

610

620

710

720

900

1000

1100

1200

1200

1500

1600

1700

SURGICAL IMPLANTS

CROSS-REFERENCE TO RELATED APPLICATIONS

This application claims the benefit of the filing date of U.S. provisional application No. 62/774,860, filed on Dec. 3, 2018, the teachings of which are incorporated herein by reference in their entirety.

BACKGROUND

Field of the Disclosure

The present disclosure relates to spinal fixation devices, orthopedic implants, intraosseous transcutaneous amputation prostheses, and other surgical implants, specifically for site-specific osseointegration of the implant and the manufacture of such implants.

Description of the Related Art

This section introduces aspects that may help facilitate a better understanding of the disclosure. Accordingly, the statements of this section are to be read in this light and are not to be understood as admissions about what is prior art or what is not prior art.

Osseointegration of surgical implants such as an orthopedic implant is an important biological process to take place for the stabilization of the implant in the body to prevent aseptic loosening and the subsequent need for a surgical revision and for an overall effective outcome for the patient for procedures that include spinal repair, knees, hips, extremities, joints, and traumatic fractures.

The body's response to an implanted material depends upon many factors including surface chemistry, surface hardness, surface texture, material composition, implant geometry as well as the location within the body. Upon introduction into the body, proteins quickly adsorb to the surface of the material. Cells sense and interact with the proteins by the use of integrins, which are surface receptors responsible for sensing the underlying layer. Integrins mediate cell adhesion by providing anchorage for cell signaling in the extracellular matrix for migration, growth, and differentiation, a fundamental cellular response to promote osseointegration of orthopedic implants. However, upon implantation of unaltered, smooth surfaces, proteins form a thin, proteinaceous layer between the biomaterial and bodily tissue that sets off a cascade of signals, resulting in the foreign body response that ultimately leads to an uncontrolled encapsulation of the unaltered biomaterial in a barrier of collagenous scar tissue, preventing intimate contact between the device and tissue, detrimental to securing orthopedic devices in place and can necessitate surgical revision of the device in the patient. Therefore, orthopedic devices developed to control soft tissue migration and create a surface that would promote hard tissue integration would prove to be beneficial for orthopedic implant device attachment to bone to properly fashion the device in place.

Titanium is one such biomaterial that is widely used for orthopedic implants due to its osteoconductive nature, that, when inserted in contact with bone, allows for bone growth onto the surface, creating direct contact between natural bone and the implant, leading to osseointegration and stable anchorage of the implant in place. The biocompatibility of titanium is attributed to a spontaneously formed, nanometer thick oxidation layer (titanium dioxide) at the surface that is porous in nature. The bone response is affected by the thickness, porosity, surface roughness values, and crystalline structure of the oxidation layer, and the relative atomic percentage of magnesium present in the titanium dioxide layer. Studies show that bone develops direct attachment to titanium with smooth surfaces or various degrees of roughness or with designed surface architecture. Porous titanium, for example, has found success in orthopedic spinal devices. Also, titanium dental implants with a microgroove surface architecture are available for enhanced osseointegration and long-term stability of the implant.

Certain plastics, polyetheretherketone (PEEK), in particular, are also used in orthopedic devices, having a modulus similar to cortical bone and having the advantages of being lighter weight, radiotransparent, and the ability to distribute mechanical load to surrounding bone to prevent stress shielding and bone recession around the implant due to the lack of adjacent bone bearing enough load to maintain health. One major shortcoming of PEEK implants is the difficulty of obtaining hard tissue cell growth onto PEEK and subsequent direct bone apposition and attachment to the PEEK implant, due to the innate surface chemistry of the plastic and hydrophobic nature of the material. Another major shortcoming is the ease with which soft tissue cells proliferate on the surface of a PEEK implant leading to fibrous encapsulation of the biomaterial. Either shortcoming or in combination create the difficulty with which to obtain osseointegration of a PEEK implant.

Several methods have been attempted to enhance direct bone ongrowth onto PEEK implants having different degrees of success including surface texturing, microgroove structures separately spaced, application of plasma spray to manipulate the surface chemistry, application of biological, inorganic, or titanium and metallic coatings, and compounding additives into the bulk plastic material. PEEK options developed for use in orthopedic devices for enhanced osseointegration include, but are not limited to, titanium-coated PEEK, PEEK with a microporous surface, PEEK with hydroxyapatite compounded into the bulk plastic, and PEEK with zeolite ceramic compounded into the material.

SUMMARY

Osseointegration of an orthopedic implant is an important step in the rehabilitation of a patient after orthopedic surgery. In successful outcomes, the process ensures anchoring of the implant in place and bone continues to remodel adjacent to the implant as the patient heals. Due to its inherent nature to osseointegrate, titanium is the predominant material used for orthopedic devices. However, the strength and modulus of titanium are greater than that of natural bone, and titanium has been found to cause degeneration of adjacent bone via stress shielding. Furthermore, titanium and metal implants are X-ray opaque, which can create challenges for surgeons to see desired bone growth adjacent to or around the implant post-operatively due to shadow artifacts around the implant misrepresenting bone growth. Also, debris from friction and wear on metal implants can cause osteolysis and systemic poisoning from metallic ions.

For these reasons, plastics have advantages for use in orthopedic implants. Plastics are X-ray transparent, allowing bone growth to be seen on and around the implant postoperatively, and plastics do not contribute to systemic poisoning from metallic ions. Certain plastics, for example, polyetheretherketone (PEEK), are also chosen for use in orthopedic implants due to their bioinertness and their strength and modulus being similar to, but less than that of natural bone. This means that a PEEK implant bearing a load will spread the load to natural tissue surrounding the implant, having the effect of inducing bone growth.

However, the surface of plastics, including PEEK, show little or no osteoconductivity. Without bone growth directly to the surface of a plastic, orthopedic implants have an inherent risk of aseptic loosening due to the body's natural immune response to form fibrous, collagenous scar tissue at the surface of the plastic implant. This soft tissue prevents intimate and direct contact of the implant and bone, further preventing bone ongrowth to the plastic surface of the implant.

PEEK and other plastic implants have the propensity for scar tissue formation surrounding the implant without osseointegration. Therefore, creating a plastic, PEEK in particular, that will osseointegrate is desirable. In an attempt to improve osseointegration of plastic implants, plastic has been altered in several ways including surface texturing, manipulation of the surface chemistry, application of biological, inorganic, or titanium and metallic coatings, application of plasma spray, and compounding additives into the bulk plastic material, but not all achieve the desired results. Coatings may absorb into the body before bone growth occurs and have the propensity to delaminate or chip off of the plastic substrate underneath, which can lead to infection and the need for corrective surgery. The compounding of additives into plastic has shown to promote bone growth to the surface of plastic, but with the propensity for bone growth only at the localized site of the additive particle at the surface of the plastic. Additives in plastic also compromise the integrity of the bulk plastic material itself, weakening the implant manufactured with this material compared to the same unaltered base plastic having no additives. Subjecting plastic to plasma spray is another method to enhance osseointegration of plastic by increasing its hydrophilic nature, but may be less effective than other methods and the surface loses its efficacy over time. Texturing the surface of plastic has been studied and shown to be an effective means to enhance osseointegration, but precise surface texture is required. A specific surface texture that showed promising effects on PEEK was microgroove geometry having undefined groove depth, groove widths ranging from 31 µm to 47 µm and groove crests ranging from 26 µm to 110 µm, exhibiting slightly oriented cell growth (mouse MC3T3-E1 preosteoblast cell line). See D. Cordero et al., "In vitro response of pre-osteoblastic cells to laser microgrooved PEEK," Biomed. Mater. 8 (2013) 055006, the teachings of which are incorporated herein by reference. These microgroove designs lack the proper dimensions to heavily influence the orientation of cell growth due to the troughs and crests being too wide to direct growth. In addition, the widths are too wide to prevent cell flattening and subsequent cell proliferation, having the effect of deficient cell differentiation and, therefore, insufficient formation of desired bone matrix. Furthermore, the trough depth is unspecified. The trough is a key factor to regulate bone growth in the direction of the channel by preventing cell spreading and migration out of the groove.

The present disclosure describes precise surface microarchitecture for osseointegration, bone growth, and bone attachment to PEEK and other plastics, for contact guidance directed bone growth, for the regeneration and connection of disrupted bone areas, and for anchoring and osseointegration of orthopedic implants. The technology permits visualization of bone growth in X-rays, retains the mechanical integrity of the bulk plastic, and does not promote stress-shielding as metal implants may. Furthermore, the described surface microarchitecture provides for bone to attach and form mechanical bonds that enhances shear-force of attached bone across the plastic and pull-force of the plastic from bone, while preventing soft tissue growth across the surface microarchitecture that can contribute to soft tissue encapsulation or soft tissue ingrowth.

Bone growth to the surface of a material is dependent upon its osteoconductive potential. Whereas titanium has a high osteoconductive potential, stainless steel has a low affinity for bone growth, and copper and silver do not conduct bone. Similarly, plastic surfaces are not inherently osteoconductive. The interaction of the body at the biomaterial interface is distinctly different for titanium, and, likewise, the cellular response on plastics is unique, requiring precise surface micro-geometry, a modification of the surface chemical functionality, or a combination of both in order to promote a positive cellular response for the growth of bone onto and in direct contact with the surface of plastics. Prior art describes improved osseointegration of titanium implants via surface modifications, but the same modifications do not guarantee equivalent outcomes on plastics.

On plastics, smooth surfaces promote cell proliferation and collagenous scar formation. This process occurs at a faster rate than the process of bone cell migration, proliferation, and differentiation to create bone matrix. In doing so, the collagenous scar tissue can overtake the surface intended for bone growth. This necessitates a modification to the surface of the plastic to create an osteoconductive surface and to inhibit the ingrowth of soft tissue cells.

Precise surface microgroove geometry on the surface of plastics prevents the proliferation of fibroblast cells and soft tissue formation across the microgrooves. In the presence of bone, oriented microgrooves inhibit infiltration of soft tissue at the bone-implant surface, essentially blocking out soft tissue cells, and allow the formation of bone in direct contact with the microgroove surface. In the environment of soft tissue and the absence of bone, the microgrooves promote attachment and growth of soft tissue parallel to the microgrooves, but inhibit soft tissue growth across the grooves. On transcutaneous implants, microgrooves oriented parallel to the skin in a circumferential fashion and present on the implant on the inner and outer layers of the skin, enhances soft tissue attachment to the microgrooves, creating a dermal seal and barrier to external contaminants, and inhibits infection from exogenous agents and downgrowth of soft tissue on the implant itself or into the body.

According to the present disclosure, the surface structure and/or chemistry of an orthopedic implant are manipulated to regulate the body's response and promote osseointegation in or around an implanted orthopedic device. The present disclosure describes manufacturing methods and surface modifications to enhance osseointegration in whole or in selected surface areas of implanted orthopedic devices and describes orthopedic devices that would benefit from bone attachment on exposed surface areas, while inhibiting fibrous tissue growth and fibrotic encapsulation.

Osteoblasts and stem cell migration and attachment are influenced via the extracellular matrix by topographical cues and surface structure of the exposed implant substrate. Surface microtexturing is a method that has been proven to be successful for osseointegration on implant surfaces by creating a complex 3-dimensional scaffold at the implant surface. On PEEK and other plastics, the present disclosure defines parallel microgroove architectures that have proven successful to promote cell adhesion, bone growth, and osseointegration. In the presence of bone, osteoblasts, or mesenchymal stem cells, the parallel microgrooves provide sites for hard tissue cell attachment and promote cell elongation within the microgrooves, permitting the cells to partially flatten and spread, which, regulates hemidesmosomal attachments of the cell to the surface of the implant substrate. The reduced attachment, in turn, inhibits cell proliferation, induces contact-guidance, a phenomenon where oriented colony structure and growth is promoted along the length of the grooves, and accelerates cellular differentiation and the creation of bone matrix. Having the proper microgroove dimensions is essential to maximize contact guidance and induce cell differentiation. In contrast, smooth, non-textured surfaces permit more cellular attachments, which triggers faster proliferation and less differentiation, and creates an affinity for fibrous encapsulation of the implant.

Simultaneously, the microgroove architecture serves to inhibit cellular migration across the grooves. In this way, an orthopedic implant can be designed for site-specific osseointegration of the entire or partial implant while orienting parallel microgrooves directionally to enhance directional bone growth for faster healing or to inhibit fibrous tissue attachment by inhibiting infiltration of soft tissue cells from migrating across the grooves. Proper microgroove dimensions are essential to influence soft tissue cells as they will easily bridge channels that are not wide enough and will spread and proliferate in troughs and upon crests that are too wide, as though the cell is recognizing an open, flat surface beneath it. Therefore, the width of the channel and width of the crest of the microgrooves themselves are important factors in order to inhibit soft tissue cell proliferation and migration across the microgrooves.

In this way, in the presence of soft tissue at the skin surface, parallel microgrooves may be oriented parallel to the surface of the skin around the circumference of a transcutaneous implant protruding through the skin in order to increase soft tissue dermal attachment to the implant. Soft tissue formation in and on the microgrooves around the circumference of the implant will create a seal and barrier to exogenous agents and inhibit downgrowth of the soft tissue formed around the transcutaneous implant.

The shape, width, depth, and periodicity of the parallel microgrooves, and interactions of cells with those parallel microgrooves, play an important role in the cellular response and ultimate ability for osseointegration of the substrate. The correct channel and crest widths will induce contact guidance and enhance cell differentiation. Laser ablation of plastic substrates to create a controlled 3-dimensional parallel microgroove architecture having a width of 8-12 micrometers (μm), a crest of 8-12 μm, and periodicity (i.e., width+crest) of 16-24 μm provides the spacing for the width of osteoblasts or mesenchymal stem cells to attach on three sides (trough bottom and two side walls), holding the cell in a spherical or ellipsoid shape, which induces cell migration in the direction of the channel and cell differentiation that leads to the formation of bone in the direction of the channel, while inhibiting the cell from flattening and spreading in an undifferentiated state. Also, the crest width of 8-12 μm is not wide enough for cell flattening and, at that width, contributes in combination with the troughs to further induce contact guidance and differentiation of osteoblasts and stem cells into hard tissue cells that excrete bone matrix. The same width, depth, and periodicity of 8-12 μm, 8-12 μm, and 16-24 μm, respectively, inhibit anti-parallel migration of soft tissue cells across the grooves, thus creating site-specific osseointegration of a PEEK spinal fusion implant device or any other orthopedic implant where microgrooves are applied to surfaces that are exposed to bone in vivo and where soft tissue growth is undesirable. Parallel microgrooves having trough and crest widths and trough depths less than 8-12 μm (e.g., 4-8 μm) will work, but are a less effective means to promote contact guidance and inhibit growth across the channels. Smaller widths than 8 μm are more easily traversed by soft tissue cells, allowing more potential for soft tissue ingrowth in sites where bone is desired. Smaller widths than 8 μm also provide less surface area for hard tissue cells to fit into a channel and adhere to the substrate, thereby inhibiting their viability.

An exposed surface refers to the exterior surface of any plastic component, whether all or in part, of a plastic implant. The exposed surface may be the external surface, an internal through hole, an indentation, an undercut, threads, macrogroove structures, or striations imparted onto the surface of the implant.

Parallel microgrooves in the size of 8-12 μm in width and 8-12 μm in depth may be formed by laser ablation, specifically using a 193 nm excimer laser. Laser-ablating a polymer surface alters the chemical nature of the surface with functional groups, enhancing the hydrophilic nature of the ablated surface, further enhancing the osteogenic nature of the surface. Laser-ablated microgrooves has a two-fold advantage of having both a chemically functional surface as well as a precisely engineered surface structure that, when placed adjacent to bone, enhances hard tissue cell differentiation, controls directional cellular and subsequent bone growth, and inhibits invasion of soft tissue that leads to encapsulation.

8-12 μm microgrooves may also be manufactured directly onto an implant via molding the surface architecture directly onto the implant or onto any implant surface structure having a 2-dimensional width greater than 8 μm. Other manufacturing methods of creating microgrooves include laser mask projection, acid etching, ion beam etching, sandblasting, micromachining, microcontact printing, photolithography, hot-pressing, hot-embossing, glanced angle deposition, and additive manufacturing (e.g., 3D printing).

The profile and dimensions of the microgrooves may be in the form of a square-wave having a width of 8 μm-12 μm, depth of 8 μm-12 μm, and crest of 8 μm-12 μm. The microgroove profile shape may be in the form having rigid corners and edges, a modified square-wave having rounded corners, troughs, and edges, a modified square-wave where the side-walls are more than 90 degrees or less than 90 degrees to the crest surface, a sinusoidal wave, or a combination of the above. The depth of the grooves and steep angle of the side walls provide a channel for the cells to differentiate or migrate within and in the direction of the channel, but inhibit the cells from migrating out of the grooves and spreading and proliferating outside of the grooves where the cells have a lesser propensity to differentiate. The channels may be arranged on an implant in a fashion to direct bone growth in the direction of the microgrooves and arranged in an anti-parallel direction in order to inhibit soft tissue ingrowth across the microgrooves.

The implant material may be any suitable, implantable grade of plastic, thermoplastic, or thermoset, including, but not limited to, PEEK (polyetheretherketone), PEKK (polyetherketoneketone), polyethylene, ultra-high molecular weight polyethylene, polypropylene, polysulfone, polyphenylsulfone, polyvinylidenefluoride, ethylenechlorotrifluoroethylene, ethylenetrifluoroethylene, polytetrafluoroethylene, polylactic acid polymer and its derivatives including, but not limited to polylactic-co-glycolic acid, polyester, polyurethane, polyetherimide, polyamide (nylon), silicone, or any compounded blend of these polymers with additives for functional mechanical integrity, additives for color, additives for radiopacity including, but not limited to barium sulfate, known bioactive osseointegration-enhancing additives including, but not limited to, calcium phosphate, hydroxyapatite, ceramic, zeolite ceramic, or zeolite ceramic infused with inorganic or metallic ions, or any other additive in the polymer for filler or otherwise. Note that some long-term catheters made with silicone could benefit from a soft tissue seal that forms on microgrooves at the catheter-skin interface.

Certain embodiments of the present disclosure may be manufactured with any implant material described above and includes the application of a coating or coatings to the surface of the substrate. Coatings include any metal, inorganic, or bioactive substance including, but not limited to titanium, calcium phosphate, hydroxyapatite, zeolite ceramic, or zeolite ceramic infused with inorganic or metallic ions. The coatings may or may not enhance osteoconduction, osteoinduction, or osseointegration and may or may not enhance connective tissue attachment. The coating may or may not enhance antimicrobial properties. The coating or coatings may be applied before or after formation of surface microgrooves.

Certain embodiments of the present disclosure may be a device composed of plastic, metal, ceramic, or any combination of the materials.

Certain embodiments of the present disclosure may be used for orthopedic applications in combination with seeding of osteoblasts, mesenchymal stem cells, or any other suitable bone-generating cell either by direct application of the cells to the surface of the microgrooves or dispersed within a bone filler that is packed within an orifice of the embodiment or secured in any way adjacent to the embodiment that allows migration of bone-forming cells from the bone filler to the microgroove surface.

Certain embodiments of the present disclosure can be implemented as:
  Spinal interbody fusion devices (spinal cages);
  Expandable spinal cages;
  Interspinous spacers;
  Suture anchors;
  Bone screws;
  Trauma plates;
  Extremity implants (including, but not limited to, toe, proximal interphalangeal (PIP), metacarpophalangeal (MCP), and carpometacarpal (CMC) finger joints);
  Hammertoe fixation devices;
  Femoral stem and acetabular components of total hip replacement devices;
  Femoral and tibial components of total knee replacement devices;
  Cranial/cranio-facial skeleton implants;
  Intraosseous transcutaneous amputation prostheses;
  Transcutaneous location of indwelling catheters;
  Transcutaneous location of K-wires; and
  Other surgical implants where osseointegration of bone or a soft tissue seal is a consideration.

BRIEF DESCRIPTION OF THE DRAWINGS

Embodiments of the disclosure will become more fully apparent from the following detailed description, the appended claims, and the accompanying drawings in which like reference numerals identify similar or identical elements.

FIG. 2 is a perspective view of a plastic spinal fusion implant, according to another embodiment of the present disclosure;

DETAILED DESCRIPTION

Detailed illustrative embodiments of the present disclosure are disclosed herein. However, specific structural and functional details disclosed herein are merely representative for purposes of describing example embodiments of the present disclosure. The present disclosure may be embodied in many alternate forms and should not be construed as limited to only the embodiments set forth herein. Further, the terminology used herein is for the purpose of describing particular embodiments only and is not intended to be limiting of example embodiments of the disclosure.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functions/acts involved.

Figure 1:
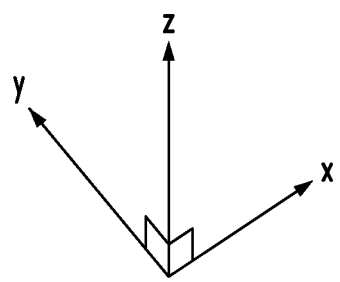
FIG. 1 is a perspective view of a plastic cervical spinal fusion implant, according to one embodiment of the present disclosure.
Figure 1:
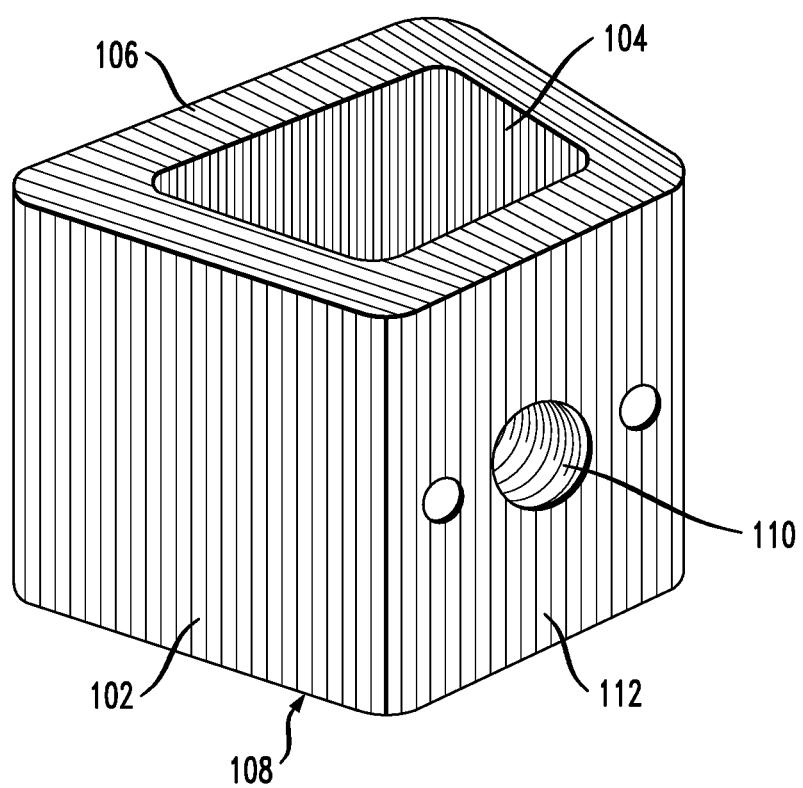

FIG. 1 is a perspective view of a plastic spinal fusion implant 100, according to one embodiment of the present disclosure. As represented in FIG. 1, the plastic implant 100 has parallel microgroove surface structures on its exterior surface 102, its interior surface 104, on its top and bottom surfaces 106 and 108. A threaded through-hole 110 is represented on the front side 112 of the implant. The parallel microgrooves on the exterior and interior surfaces 102 and 104 are parallel to the z axis, while the microgrooves on the top surface 106 and the microgrooves (not shown in FIG. 1) on the bottom surface 108 are parallel to the y axis.

The parallel alignment of the microgrooves promote contact guidance, bone growth in the direction of the microgrooves. The microgrooves parallel to the z axis promote contact guidance from adjacent vertebrae (not shown in FIG. 1) located at the top and bottom of the plastic implant 100 and in direct contact with the implant after implantation. The microgrooves are shown to cover the entire exposed outer-facing area of the implant. The parallel microgroove pattern on the interior surface 104 directs bone growth into the interior of the implant from vertebrae in direct contact with the implant. During the implant procedure, the interior of the implant is often filled with bone filler material, which may have stem cells or osteoblasts distributed within the material prior to implantation. When stem cells or osteoblasts are present in the bone filler or present otherwise in the interior of the implant, the microgrooves on the interior surface 104 provide means for cells to be seeded, then differentiate, then grow bone from the interior of the implant out towards the adjacent vertebrae in direct contact with the implant.

FIG. 2 is a perspective view of a plastic spinal fusion implant 200, according to another embodiment of the present disclosure. The plastic implant 200 is similar to the plastic implant 100 of FIG. 1, with analogous surfaces having similar labels, except that, in the plastic implant 200, the top and bottom surfaces 206 and 208 have concentric parallel microgroove structures that are parallel to the xy-plane. Like the parallel microgrooves on the top and bottom surfaces 106 and 108 of FIG. 1, these concentric microgrooves on the top and bottom surfaces 206 and 208 promote bone regeneration from the adjacent vertebra (not shown). The concentric microgrooves on the top and bottom surfaces 206 and 208 inhibit soft tissue cells from entering, adhering to, and proliferating on the top and bottom surfaces 206 and 208 of the implant 200 post-implantation. Note that, in this case, the microgrooves on the top and bottom surfaces 206 and 208 of the implant are orthogonal to the microgrooves on the exterior surface 202 of the implant.

Figure 3:
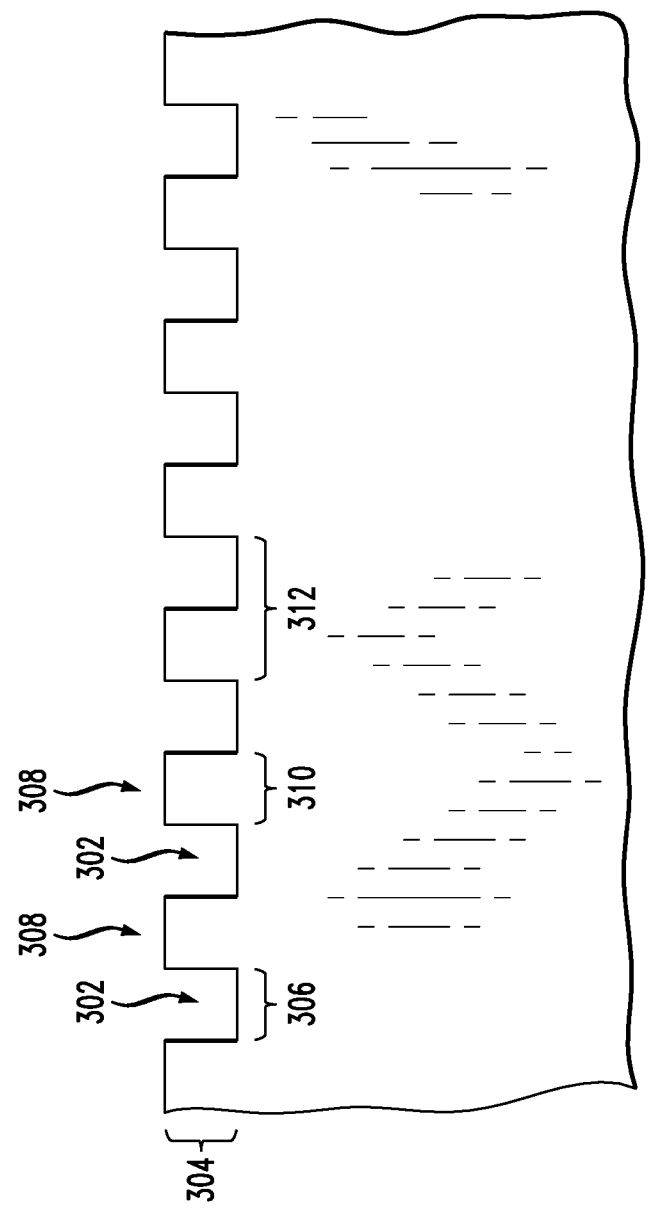
FIG. 3 is a cross-sectional side view of a portion of the microgroove structure on any of the surfaces of the implants of FIGS. 1 and 2 (as well as FIGS. 4-20)

FIG. 3 is a cross-sectional side view of a portion of the microgroove structure on any of the surfaces of the implants 100 and 200 of FIGS. 1 and 2 (as well as FIGS. 4-20). As ideally represented in FIG. 3, the microgroove structure comprises grooves (i.e., troughs, channels) 302 having depth 304 and width 306 separated by ridges (i.e., crests) 308 having width 310. In certain implementations, the grooves 302 are 10 µm+/−2 µm deep, and the grooves 302 and crests 308 are both 10 µm+/−2 µm wide such that the periodicity (i.e., pitch) 312 of the grooves is 20 µm+/−4 µm. The grooves may be in the form of a square-wave with rigid corners and edges, a modified square-wave having rounded corners and edges, a modified square wave where the side-walls are more than 90 degrees or less than 90 degrees to the crest surface, or a combination of the above.

In one implementation, the microgroove structure is formed using a 193 nm ArF excimer laser to ablate a smooth plastic surface. Organic compounds (plastics) tend to absorb the ultraviolet light of the excimer laser and enable the ablation to happen. Other types of excimer lasers having wavelengths ranging from 126 nm to 351 nm might also be used to ablate the surface of plastics. In addition, it may be possible to use other types of lasers that are not within the excimer class of lasers to ablate the surface of plastic materials to create microgroove structures.

Furthermore, applying a coating onto the plastic surface could enhance or enable the ablation of the plastic with a laser that otherwise would not be absorbed by the plastic. For example, Crysta-Lyn Chemical Company of Binghamton, N.Y., manufactures Clearweld coatings that enable laser-welding of plastics that are transparent to the laser. Such coatings may be able to enhance laser-ablation if using a type of laser that would not typically do so (i.e., a laser that is not absorbed by the plastic material). This same company also manufactures a version that is not coated onto the surface, but is compounded into the plastic to absorb the laser energy to heat up the plastic for welding plastic pieces together. It could potentially be possible that this or another compound could enable laser ablation of plastics when that type of laser would normally not do so.

According to another implementation, the microgroove structures could be formed by manufacturing the plastic components by injection molding. A subset of injection molding is called micromolding to manufacture small parts or small features on a part. This process can get down to below 10 µm, so, in theory, it could be possible to micromold microgrooves.

According to yet another implementation, the microgroove structures could be formed using a hot blade press or hot wire contraption that is precisely pressed into or dragged along and into a plastic surface.

In orthopedic devices, parallel microgrooves create a specific location for the device to osseointegrate. The microgrooves not only enhance bone growth, but also provide channels for directional growth. In this manner, bone being formed from both ends of a groove can grow towards the center to meet somewhere in the middle of that groove or if bone begins on one end, it can continue to grow to the other end of the microgroove, ultimately creating bone on the device for the length of the groove. The parallel microgrooves also provide a 3-dimensional surface structure for bone to grow into and form a mechanical bond, creating a greater force for the device to be pulled from surrounding bone. For example, bone formation in circumferential parallel microgrooves on a rod-shaped device that is inserted into bone will have an increased pull-out force due to not only the bone ongrowth to the surface, but also due to the ingrowth into the grooves.

Simultaneously, the microgrooves on a device inhibit soft tissue cells from crossing over the grooves, spreading, proliferating, and forming scar tissue. It can be important for the exterior of an orthopedic device to have microgrooves oriented properly to inhibit soft tissue from spreading into the bone-contacting area of the device, further allowing more time for bone to grow and anchor the device into place.

While soft tissue cells are inhibited from crossing the grooved surface, soft tissue cells will proliferate and spread on the crests and troughs and in the orientation of the grooves and form scar tissue. This is advantageous for implants protruding through skin needing a sealed barrier from outside the skin to inside the stoma. Parallel microgrooves oriented circumferentially around the device protruding through the skin provide a localized site on the implant for soft tissue to adhere and create a seal within the grooves around the implant, while inhibiting ingrowth across the grooves down into the stoma. Devices benefiting from a transcutaneous seal include long-term catheters, K-wires, and intraosseous transcutaneous amputation prostheses.

Parallel microgrooves can be used in the design of intraosseous transcutaneous amputation prostheses or to create a skin barrier of other long-term or short-term transcutaneous medical devices. The use of parallel microgrooves arranged on a transcutaneous implant parallel to and located on the exterior and interior of the skin surface will create a seal and barrier to exogenous agents, encourage and enhance the dermal attachment at the skin-implant interface, and prevent or reduce the occurrence of epithelial downgrowth and the ensuing infection.

Figure 4:
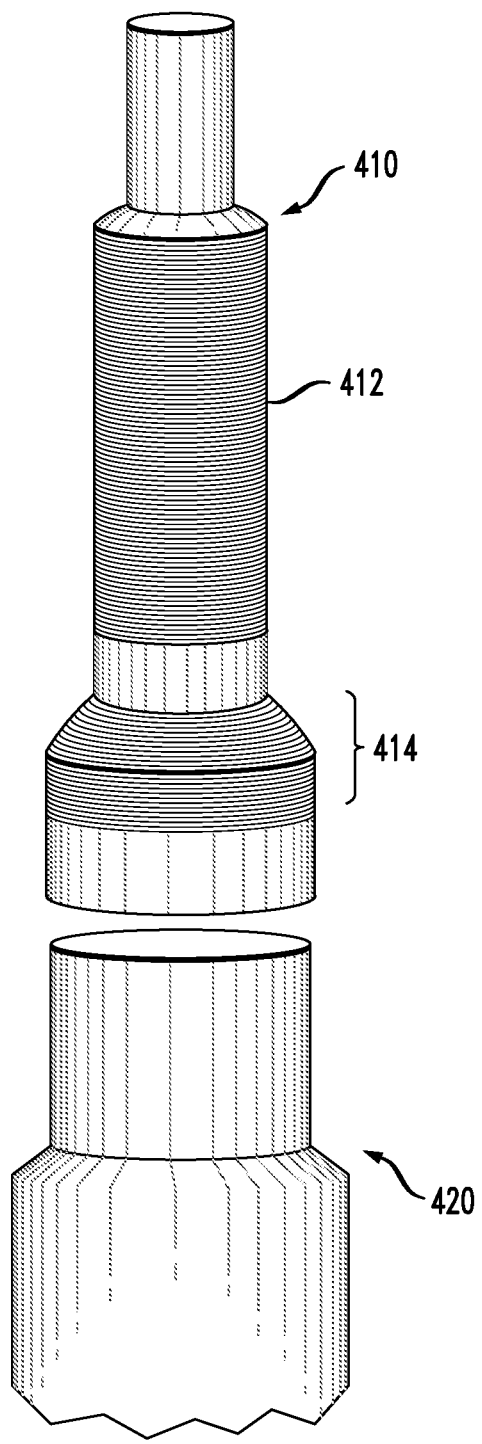
FIG. 4 is a perspective view of an intraosseous transcutaneous amputation prosthesis, according to another embodiment of the present disclosure.

FIG. 4 is a perspective view of an intraosseous transcutaneous amputation prosthesis 400 having a proximal component 410 and a distal component 420, according to another embodiment of the present disclosure. As shown in FIG. 4, the proximal component 410 has (i) an intramedullary portion 412 with parallel microgrooves oriented circumferentially to promote bone growth and increase pull-out force by forming mechanical bonding from bone formation in the grooves and (ii) a portion 414 protruding through the skin with parallel microgrooves oriented circumferentially to induce contact guidance for soft tissue around the device, promote soft tissue attachment, inhibit ingrowth of soft tissue into the stoma, and create a seal between the soft tissue and the device 400. The distal component 420 is an external complementary attachment to the proximal component 410.

Figure 5:
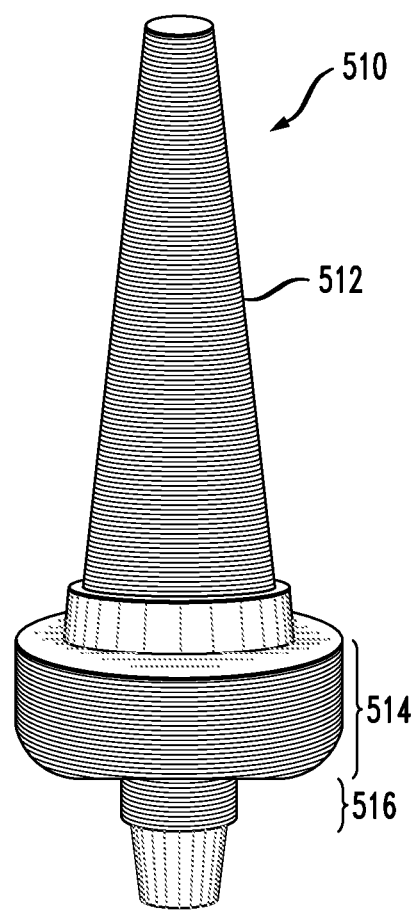
FIG. 5 is a perspective view of a component for an intraosseous transcutaneous amputation prosthesis, according to another embodiment of the present disclosure.

FIG. 5 is a perspective view of a proximal component 510 for an intraosseous transcutaneous amputation prosthesis, according to another embodiment of the present disclosure. As shown in FIG. 5, like the proximal component 410 of FIG. 4, the proximal component 510 has (i) an intramedullary portion 512 with parallel microgrooves oriented circumferentially to promote bone growth and increase pull-out force by forming mechanical bonding from bone formation in the grooves and (ii) a portion 516 protruding through the skin with parallel microgrooves oriented circumferentially to induce contact guidance for soft tissue around the device, promote soft tissue attachment, inhibit ingrowth of soft tissue into the stoma, and create a seal between the soft tissue and the device 510. In addition, the proximal component 510 has an intermediate portion 514 below skin level with parallel microgrooves oriented circumferentially to provide more area for soft tissue attachment to create a seal and also prevent ingrowth of soft tissue across the grooves. Note that a distal component analogous to the distal component 420 of FIG. 4 may be an external complementary attachment to the proximal component 510.

Figure 6A:
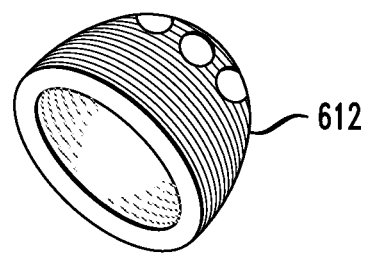
FIGS. 6A and 6B are respective perspective views of an acetabular component and a femoral stem component for a total hip replacement device, according to another embodiment of the disclosure.
Figure 6B:
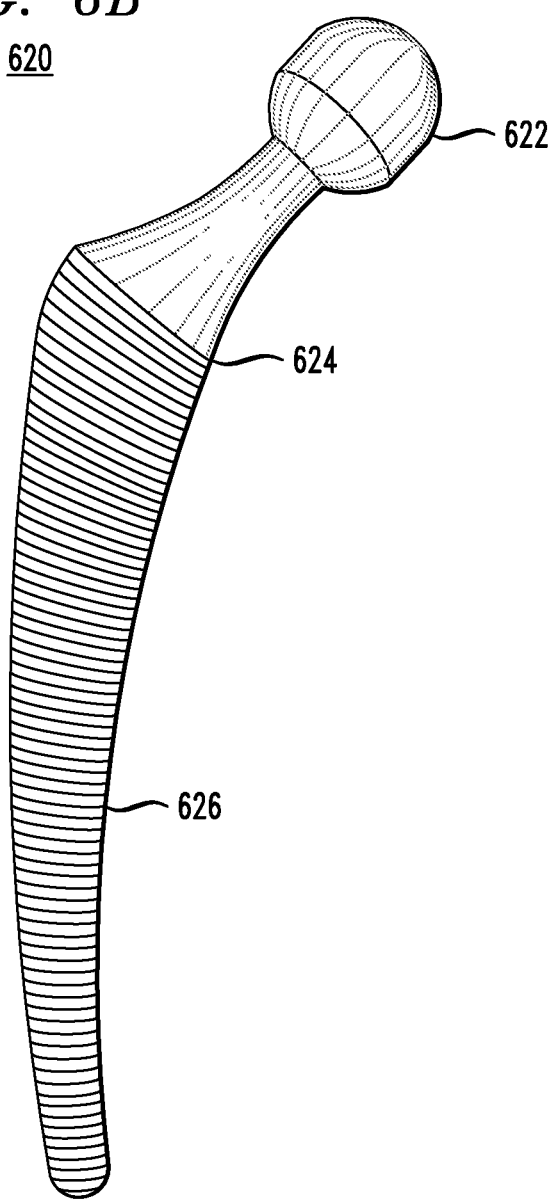

FIGS. 6A and 6B are respective perspective views of an acetabular component 610 and a femoral stem component 620 for a total hip replacement device, according to another embodiment of the disclosure. As shown in FIG. 6A, the acetabular component 610 has an exterior surface 612 with parallel microgrooves oriented circumferentially to inhibit soft tissue ingrowth while also promoting bone growth and increasing pull-out force by creating a mechanical bond from bone formation in the grooves. As shown in FIG. 6B, the femoral step component 620 has a femoral head 622, parallel microgrooves 624 oriented circumferentially near the insertion point to inhibit soft tissue downgrowth, and a femoral stem 626 with microgrooves oriented circumferentially to enhance pull-out force.

Figure 7A:
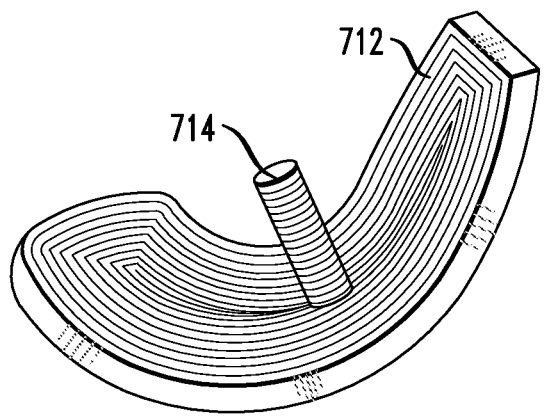
FIGS. 7A and 7B are respective perspective views of a femoral component and a tibial component of a total knee prosthesis, according to another embodiment of the disclosure.
Figure 7B:
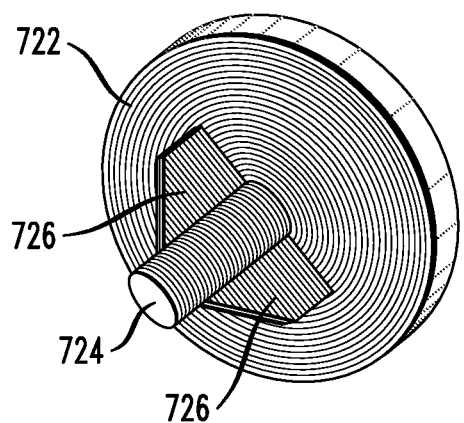

FIGS. 7A and 7B are respective perspective views of a femoral component 710 and a tibial component 720 of a total knee prosthesis, according to another embodiment of the disclosure. As shown in FIG. 7A, the femoral component 710 has parallel microgrooves oriented in a concentric pattern on the bone-contacting side 712 to enhance bone growth between the femur and the femoral component 710 and to inhibit soft tissue ingrowth from the outside in. The femoral component 710 has a pin 714 with parallel microgrooves oriented circumferentially to enhance pull-out force. FIG. 7B shows a view of the bottom of the tibial component 720, which has direct contact with bone. The bottom surface 722 of the tibial component 720 has microgrooves oriented concentrically to inhibit soft tissue ingrowth while promoting bone growth to the tibia. The tibial component 720 has a pin 724 with microgrooves oriented circumferentially and wings 726 with parallel microgrooves oriented longitudinally to promote bone growth and create a mechanical bond to increase pull-out force.

Figure 8A:
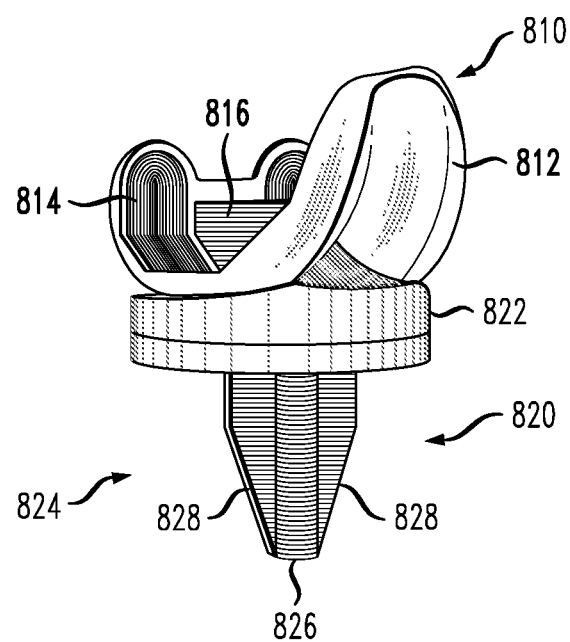
FIG. 8A is a perspective view of a total knee prosthesis, according to another embodiment of the disclosure.
Figure 8B:
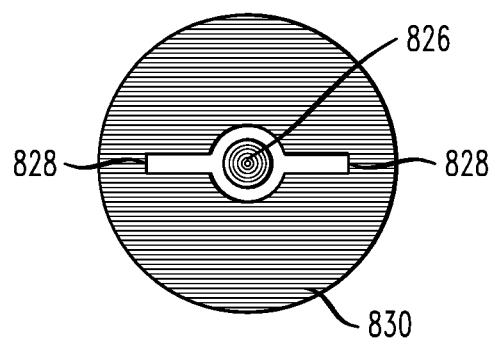
FIG. 8B is a view of the bottom of the tibial component of FIG. 8A.

FIG. 8A is a prospective view of a total knee prosthesis HQ having a femoral component 810 and a tibial component 820, according to another embodiment of the disclosure. FIG. 8B is a view of the bottom of the tibial component 820 of FIG. 8A. As shown in FIGS. 8A and 8B, the femoral component 810, which rocks on the plastic bearing 822 of the tibial component 820, has a smooth outer surface 812 that contacts the bearing 822. As shown in FIG. 8A, the interior surface 814 of the femoral component 810, which has direct contact with bone, has microgrooves oriented to promote bone growth and fixation of the femoral component 810. In addition, the bar 816 of the femoral component 810, which extends into a groove cut into the femur, has parallel microgrooves oriented longitudinally to promote bone growth and into the grooves and increase pull-out force. As shown in FIGS. 8A and 8B, the stem 824 of the tibial component 820, which extends into the tibia, has a pin 826 with parallel microgrooves oriented circumferentially and wings 828 with parallel microgrooves oriented longitudinally to create a mechanical bond with bone and increase pull-out force. As shown in FIG. 8B, the bottom surface 830 of the tibial component 820, which makes direct contact with bone, has parallel microgrooves to enhance bone growth to the device.

Figure 9:
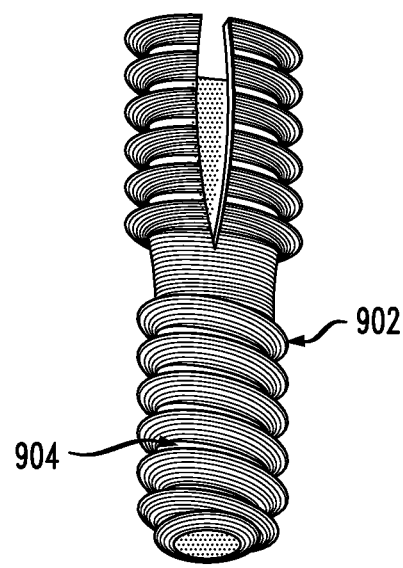
FIG. 9 is a perspective view of a hammertoe fixation device, according to another embodiment of the disclosure.

FIG. 9 is a perspective view of a hammertoe fixation device 900, according to another embodiment of the disclosure. As shown in FIG. 9, the hammertoe fixation device 900 has parallel microgrooves formed in a spiral on both the thread 902 and the shaft 904 of the device.

Figure 10:
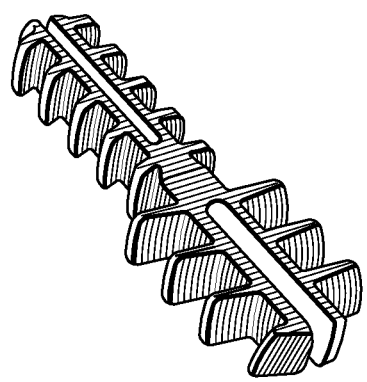
FIG. 10 is a perspective view of a hammertoe fixation device, according to another embodiment of the disclosure.

FIG. 10 is a perspective view of a hammertoe fixation device 1000, according to another embodiment of the disclosure. As shown in FIG. 10, the exterior surface of the device 1000 has microgrooves to be in direct contact with bone to enhance bone growth and osseointegration and provide a mechanical fixation from bone in the microgrooves thereby increasing the pull-out force.

Figure 11:
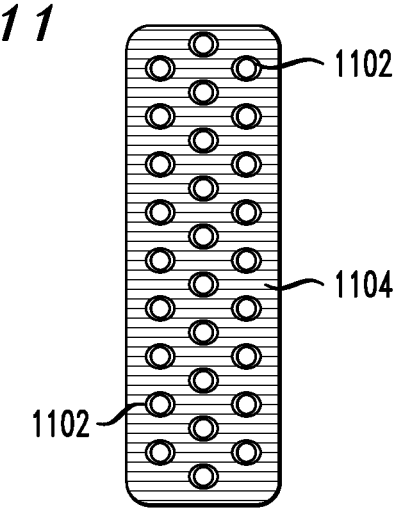
FIG. 11 is a bottom view of a trauma plate, according to another embodiment of the disclosure.

FIG. 11 is a bottom view of a trauma plate 1100 having through holes 1102 for screws, according to another embodiment of the disclosure. As shown in FIG. 11, the bottom surface 1104 of the trauma plate 1100, which has direct contact with bone, has parallel microgrooves to enhance bone growth directly to the surface of the plate 1100 providing fixation of the plate 1100 to bone.

Figure 12A:
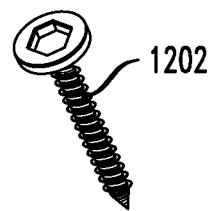
FIG. 12A is a perspective view of a bone screw, according to another embodiment of the disclosure.
Figure 12B:
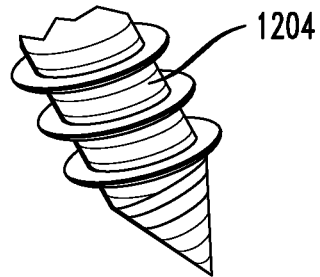
FIG. 12B is a magnified perspective view of the distal end of the (threaded) shank of the bone screw of FIG. 12A.

FIG. 12A is a perspective view of a bone screw 1200, according to another embodiment of the disclosure. FIG. 12B is a magnified perspective view of the distal end of the (threaded) shank 1202 of the bone screw 1200 of FIG. 12A. As shown in FIG. 12B, the bone screw 1200 has spiral microgrooves on the screw shaft 1204.

Figure 13:
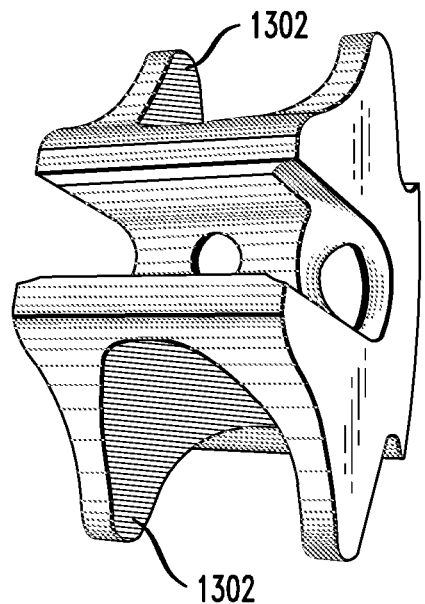
FIG. 13 is a perspective view of an interspinous spacer, according to another embodiment of the disclosure.

FIG. 13 is a perspective view of an interspinous spacer 1300, according to another embodiment of the disclosure. As shown in FIG. 13, the interior surfaces 1302 of interspinous spacer 1300, which have direct contact with bone, have parallel microgrooves oriented longitudinally to enhance osseointegration of the device and provide a mechanical bond for increasing separation force in the up and down directions.

Figure 14:
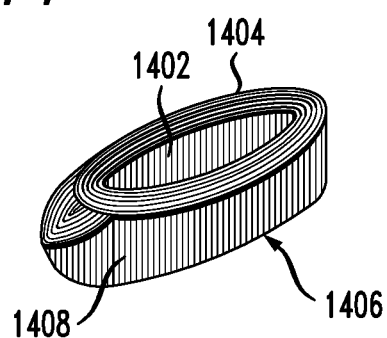
FIG. 14 is a perspective view of a spinal interbody fusion device, according to another embodiment of the disclosure.

FIG. 14 is a perspective view of a lumbar spinal interbody fusion device 1400, according to another embodiment of the disclosure. This embodiment contains a through-growth region through the center of the device for bone to form and fuse the vertebrae above and below the device. The embodiment is designed with microgroove architecture to conduct and encapsulate the device in bone to anchor the device in place and promote bone growth in the through-growth region as well as the device exterior. As shown in FIG. 14, the interior surface 1402 of the device has parallel microgrooves oriented longitudinally to induce contact guidance and conduct bone growth from top down and bottom up in the through-growth region of the device. The design of the top and bottom surfaces 1404 and 1406 of the device has microgrooves oriented circumferentially to enhance bone growth directly to the surface of the device while inhibiting soft tissue ingrowth from the device exterior in towards the center across the microgrooves. The exterior side surface 1408 of the device is designed with parallel microgrooves oriented longitudinally to induce contact guidance and conduct bone from top down and bottom up from the adjacent vertebrae in direct contact with the device above and below.

Figure 15:
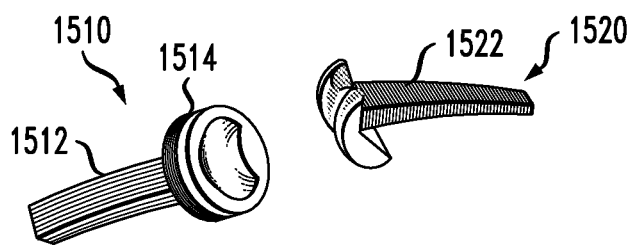
FIG. 15 is a perspective view of a PIP finger joint device, according to another embodiment of the disclosure.

FIG. 15 is a perspective view of the proximal and distal components 1510 and 1520 of a PIP finger joint device 1500, according to another embodiment of the disclosure. As shown in FIG. 15, the stem 1512 of the proximal component 1510 has parallel microgrooves oriented longitudinally, while the outer surface of the bearing 1514 of the proximal component 1510 has parallel microgrooves oriented circumferentially. In addition, the stem 1522 of the distal component 1520 has parallel microgrooves oriented circumferentially for greater pull-out force.

Figure 16:
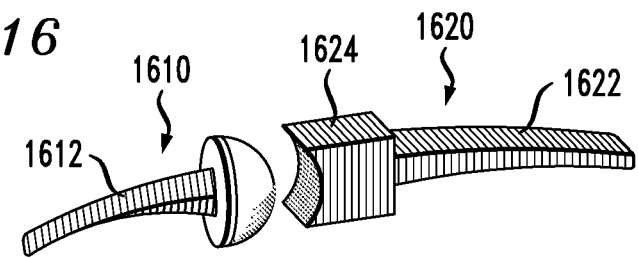
FIG. 16 is a perspective view of an MCP finger joint device, according to another embodiment of the disclosure.

FIG. 16 is a perspective view of the proximal and distal components 1610 and 1620 of an MCP finger joint device 1600, according to another embodiment of the disclosure. As shown in FIG. 16, the stem 1612 of the proximal component 1610 has parallel microgrooves oriented circumferentially. In addition, the stem 1622 and the outer surface of the bearing 1624 of the distal component 1620 have parallel microgrooves oriented circumferentially.

Figure 17:
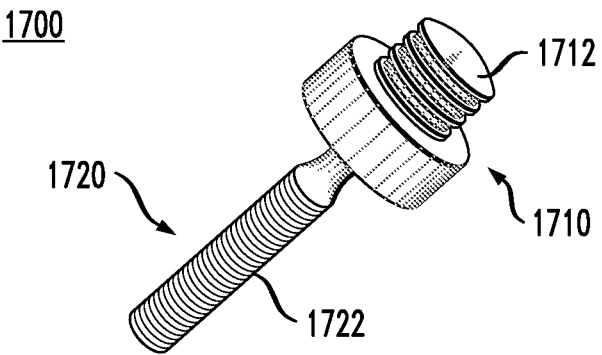
FIG. 17 is a perspective view of a CMC finger joint device, according to another embodiment of the disclosure.

FIG. 17 is a perspective view of the proximal and distal components 1710 and 1720 of a CMC finger joint device 1700, according to another embodiment of the disclosure. As shown in FIG. 17, the stem 1712 of the proximal component 1710 and the stem 1722 of the distal component 1720 both have parallel microgrooves oriented circumferentially to enhance pull-out force.

Figure 18:
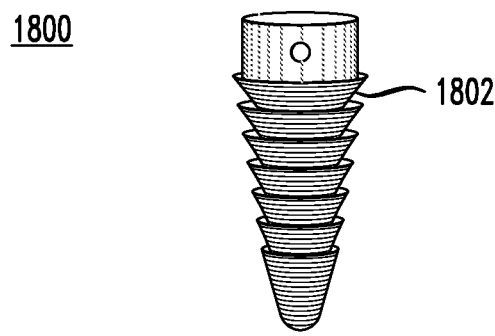
FIG. 18 is a perspective view of a suture anchor, according to another embodiment of the disclosure.

FIG. 18 is a perspective view of a suture anchor 1800, according to another embodiment of the disclosure. As shown in FIG. 18, the anchor shaft 1802 has parallel microgrooves oriented circumferentially to enhance osseointegration and provide mechanical fixation to bone to increase pull-out force.

Figure 19:
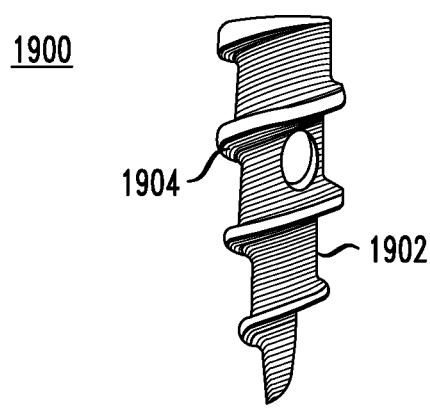
FIG. 19 is a perspective view of a suture anchor, according to another embodiment of the disclosure.

FIG. 19 is a perspective view of a suture anchor 1900, according to another embodiment of the disclosure. As shown in FIG. 19, the anchor shaft 1902 as well as the top and bottom surfaces of the spiral anchor thread 1904 have spiral microgrooves oriented circumferentially to enhance bone growth and osseointegration and to provide mechanical fixation to increase pull-out force.

Figure 20:
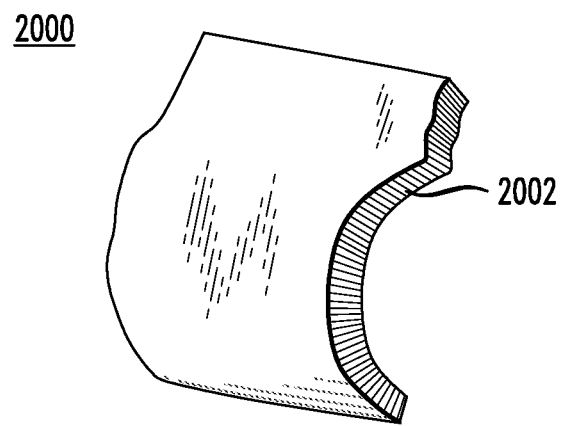
FIG. 20 is a perspective view of a cranial implant, according to another embodiment of the disclosure.

FIG. 20 is a perspective view of a cranial implant 2000, according to another embodiment of the disclosure. As shown in FIG. 20, the side wall 2002 of the cranial implant 2000, which is in direct contact with bone, has parallel microgrooves oriented longitudinally to promote bone growth onto the device from adjacent bone.

Although the disclosure contains figures showing specific types of surgical implants having microgrooves on specific surfaces having specific orientations, those skilled in the art will understand that other embodiments of the disclosure include other suitable types of surgical implants as well as surgical implants having microgrooves on other surfaces and/or with different orientations than those shown in the figures.

As used herein, the term "concentric" refers to microgrooves that are nested inside one another on an implant surface, such as, for example, on surface 206 of FIG. 2, on surface 712 of FIG. 7A, on surface 722 of FIG. 7B, and on surface 1404 of FIG. 14. As used herein, the term "circumferential" refers to microgrooves that form closed paths around an implant, such as, for example, on surfaces 412 and 414 of FIG. 4, on surfaces 512, 514, and 516 of FIG. 5, and surfaces 1802 of FIG. 18. As used herein, the term "spiral" refers to microgrooves that form spiral paths around an implant, such as, for example, on surfaces 902 and 904 of FIG. 9, on surface 1204 of FIG. 12B, and on surfaces 1902 and 1904 of FIG. 19. As used, herein, the term "longitudinal" refers to linear microgrooves, such as, for example, on surfaces 102 and 106 of FIG. 1, on surface 202 of FIG. 2, on surfaces 726 of FIG. 7, on surface 830 of FIG. 8, on surface 1104 of FIG. 11, and on surface 1408 of FIG. 14. In each of these situations and possibly other situations, sets of adjacent microgrooves that do not intersect are said to be "parallel" to one another.

In certain embodiments of the disclosure, a surgical implant comprises a plastic component having an exposed surface, wherein at least a portion of the exposed surface has a plurality of parallel microgrooves that enhance bone growth and osseointegration with adjacent bone and, after the osseointegration, increase pull-out force of the surgical implant from the adjacent bone, wherein the microgrooves have widths of less than or equal to 12 micrometers, depths of less than or equal to 12 micrometers, crests of less than or equal to 12 micrometers, and a periodicity of less than or equal to 24 micrometers.

In certain embodiments of one or more of the above, the plastic component is the surgical implant.

In certain embodiments of one or more of the above, the surgical implant further comprises a non-plastic component connected to the plastic component.

In certain embodiments of one or more of the above, the plastic component is made of polyetheretherketone (PEEK).

In certain embodiments of one or more of the above, after the surgical implant has been implanted, the portion of the exposed surface having the plurality of parallel microgrooves is in direct contact with bone.

In certain embodiments of one or more of the above, the plurality of parallel microgrooves are oriented perpendicular to the pull-out direction from the bone.

In certain embodiments of one or more of the above, a second portion of the exposed surface has a second plurality of parallel microgrooves; and, after the surgical implant has been implanted, the second portion of the exposed surface of the surgical implant is adjacent to an exposed surface of the bone.

In certain embodiments of one or more of the above, the second plurality of parallel microgrooves are oriented longitudinally toward the bone.

In certain embodiments of one or more of the above, after the surgical implant has been implanted, the portion of the exposed surface of the surgical implant is adjacent to an exposed surface of the bone.

In certain embodiments of one or more of the above, the plurality of parallel microgrooves are oriented longitudinally toward the bone.

In certain embodiments of one or more of the above, the portion of the exposed surface is an exterior surface of the surgical implant.

In certain embodiments of one or more of the above, the portion of the exposed surface is an interior surface of the surgical implant.

In certain embodiments of one or more of the above, the microgrooves have widths of 4-12 micrometers, depths of 4-12 micrometers, crests of 4-12 micrometers, and a periodicity of 8-24 micrometers.

In certain embodiments of one or more of the above, the microgrooves have widths of 8-12 micrometers, depths of 8-12 micrometers, crests of 8-12 micrometers, and a periodicity of 16-24 micrometers.

In certain embodiments of one or more of the above, the surgical implant further comprises a smooth portion of the exposed surface without microgrooves.

In certain embodiments of one or more of the above, the plurality of parallel microgrooves are oriented concentrically on the portion of the exposed surface.

In certain embodiments of one or more of the above, the plurality of parallel microgrooves are oriented longitudinally on the portion of the exposed surface.

In certain embodiments of one or more of the above, the plurality of parallel microgrooves are oriented circumferentially on the portion of the exposed surface.

In certain embodiments of one or more of the above, the plurality of parallel microgrooves are oriented spirally on the portion of the exposed surface.

In certain embodiments of one or more of the above, the surgical implant is a transcutaneous implant having a portion that, after the surgical implant has been implanted, protrudes through the skin; and the plurality of parallel microgrooves are oriented circumferentially below the skin surface to induce contact guidance for soft tissue around the surgical implant, promote soft tissue attachment, inhibit ingrowth of soft tissue into stoma, and create a seal between the soft tissue and the surgical implant.

In certain embodiments of one or more of the above, the plurality of parallel microgrooves are configured to inhibit soft tissue ingrowth across the microgrooves, inhibit scar tissue formation where bone is needed to regenerate, and induce contact guidance to promote bone growth along the microgrooves.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this disclosure may be made by those skilled in the art without departing from embodiments of the disclosure encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the disclosure.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

All documents mentioned herein are hereby incorporated by reference in their entirety or alternatively to provide the disclosure for which they were specifically relied upon.

Reference herein to "one embodiment" or "an embodiment" means that a particular feature, structure, or characteristic described in connection with the embodiment can be included in at least one embodiment of the disclosure. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

As used herein and in the claims, the term "provide" with respect to an apparatus or with respect to a system, device, or component encompasses designing or fabricating the apparatus, system, device, or component; causing the apparatus, system, device, or component to be designed or fabricated; and/or obtaining the apparatus, system, device, or component by purchase, lease, rental, or other contractual arrangement.

Unless otherwise specified herein, the use of the ordinal adjectives "first," "second," "third," etc., to refer to an object of a plurality of like objects merely indicates that different instances of such like objects are being referred to, and is not intended to imply that the like objects so referred-to have to be in a corresponding order or sequence, either temporally, spatially, in ranking, or in any other manner.

What is claimed is:

1. A surgical implant comprising a plastic component having an exterior side surface, an interior side surface, a top surface, and a bottom surface, wherein:
   each of the exterior and interior side surfaces has a plurality of vertical, elongated microgrooves and each of the top and bottom surfaces has a plurality of concentric, elongated microgrooves, wherein the vertical and concentric, elongated microgrooves are configured to enhance bone growth and osseointegration with adjacent bone and, after the osseointegration, increase pull-out force of the surgical implant from the adjacent bone, wherein:
   each pair of adjacent, elongated microgrooves running along the exterior side surface from the top surface to the bottom surface is separated by a single, contiguous, elongated crest running from the top surface to the bottom surface;
   each pair of adjacent, elongated microgrooves running along the interior side surface from the top surface to the bottom surface is separated by a single, contiguous, elongated crest running from the top surface to the bottom surface; and
   the elongated microgrooves have widths of less than or equal to 12 micrometers, depths of less than or equal to 12 micrometers, crest widths of less than or equal to 12 micrometers, and a periodicity of less than or equal to 24 micrometers, wherein:
      after the surgical implant has been implanted, the top and bottom surfaces are configured to be in direct contact with bone; and
      the vertical and concentric, elongated microgrooves are configured to inhibit soft tissue ingrowth across the elongated microgrooves, inhibit scar tissue formation where bone is needed to generate, and induce contact guidance to promote bone growth in the direction of the elongated microgrooves.

2. The surgical implant of claim 1, wherein the plastic component is the surgical implant.

3. The surgical implant of claim 1, wherein the surgical implant further comprises a non-plastic component connected to the plastic component.

4. The surgical implant of claim 1, wherein the plastic component is made of polyetheretherketone (PEEK).

5. The surgical implant of claim 1, wherein the elongated microgrooves have widths of 4-12 micrometers, depths of 4-12 micrometers, crest widths of 4-12 micrometers, and a periodicity of 8-24 micrometers.

6. The surgical implant of claim 5, wherein the elongated microgrooves have widths of 8-12 micrometers, depths of 8-12 micrometers, crest widths of 8-12 micrometers, and a periodicity of 16-24 micrometers.

7. The surgical implant of claim 1, wherein the surgical implant is a spinal fusion implant.

8. The surgical implant of claim 7, wherein the spinal fusion implant is a cervical spinal fusion implant.

9. The surgical implant of claim 7, wherein the surgical fusion implant is a lumbar spinal interbody fusion implant.

10. The surgical implant of claim 1, wherein the surgical implant further comprises a threaded through-hole between the exterior and interior side surfaces.

11. The surgical implant of claim 1, wherein:
   each pair of adjacent, elongated microgrooves running around the top surface is separated by a single, contiguous, elongated crest running around the top surface; and
   each pair of adjacent, elongated microgrooves running around the bottom surface is separated by a single, contiguous, elongated crest running around the bottom surface.

* * * * *